(12) United States Patent
Zang et al.

(10) Patent No.: US 7,828,818 B2
(45) Date of Patent: Nov. 9, 2010

(54) HEART SEPTAL DEFECT OCCLUSION DEVICES WITH ADJUSTABLE LENGTH TETHER ADAPTING TO THE UNIQUE ANATOMY OF THE PATIENT

(75) Inventors: Shixian Zang, Shenzhen (CN); Eirc Zi, Shenzhen (CN); Shiwen Lv, Shenzhen (CN); Yaoting Feng, Shenzhen (CN); Yuehui Xie, Shenzhen (CN)

(73) Assignee: Lifetech Scientific Inc., Shenzhen (CN)

( * ) Notice: Subject to any disclaimer, the term of this patent is extended or adjusted under 35 U.S.C. 154(b) by 641 days.

(21) Appl. No.: 11/307,178

(22) Filed: Jan. 26, 2006

(65) Prior Publication Data

US 2006/0200196 A1    Sep. 7, 2006

(30) Foreign Application Priority Data

Jan. 28, 2005    (CN) .................. 2005 1 0032924

(51) Int. Cl.
*A61B 17/08* (2006.01)
(52) U.S. Cl. ...................................... 606/213
(58) Field of Classification Search ............ 606/1, 606/131, 151, 200, 213; 623/2.2, 2.23–25, 623/23.72; 128/830, 831, 832
See application file for complete search history.

(56) References Cited

U.S. PATENT DOCUMENTS 3,874,388 A     4/1975 King et al.
5,451,235 A  *  9/1995 Lock et al. ................. 606/213
5,683,411 A  * 11/1997 Kavteladze et al. ........ 606/200
5,944,738 A  *  8/1999 Amplatz et al. ............ 606/213
6,712,836 B1 *  3/2004 Berg et al. .................. 606/213
7,144,410 B2 * 12/2006 Marino et al. .............. 606/213
7,658,748 B2 *  2/2010 Marino et al. .............. 606/213
2004/0117032 A1  6/2004 Roth
2005/0065547 A1*  3/2005 Marino et al. .............. 606/213

FOREIGN PATENT DOCUMENTS

| CN | 2430113 | 5/2001 |
| CN | 2566817 | 8/2003 |
| CN | 1442122 | 9/2003 |
| CN | 2661130 | 12/2004 |
| WO | WO 2005/034738 A | 4/2005 |

* cited by examiner

*Primary Examiner*—(Jackie) Tan-Uyen T Ho
*Assistant Examiner*—Alexander Orkin
(74) *Attorney, Agent, or Firm*—Raymond Sun

(57) ABSTRACT

The present invention relates to heart septal defect occlusion devices with adjustable length tether which can adapt the interseptal length of the device to the unique anatomy of the patient. The right disc as recited in the present invention is made from a double-deck metal mesh with contraction function, and the left disc is made from at least two skeletons covered by membranes. The two discs are active linked together. Because the connection of the two discs has gimbal function and the distance between the two discs may expand and contract suitably, the device can adapt to the unique anatomy of the patient. Therefore the two discs may attach to the heart valves closely and increase its closing ability. Furthermore it can reduce the thrombus and operate more easily.

17 Claims, 4 Drawing Sheets

HEART SEPTAL DEFECT OCCLUSION DEVICES WITH ADJUSTABLE LENGTH TETHER ADAPTING TO THE UNIQUE ANATOMY OF THE PATIENT

CROSS REFERENCE TO RELATED APPLICATION

This application claims the benefit of a Chinese patent application No. 20051 0032924.0 (CN), filed on Jan. 28, 2005.

TECHNICAL FIELD

The present invention relates to an occlusion device for treating congenital heart disease, such as patent foramen ovale (PFO), atrial septal defect (ASD), patent ductus arteriosus (PDA) or ventricular septal defect (VSD), etc.

BACKGROUND OF THE INVENTION

Congenital heart diseases include patent foramen ovale (PFO), atrial septal defect (ASD), patent ductus arteriosus (PDA) and ventricular septal defect (VSD), etc. PFO and ASD are openings in the wall between the right atrium and left atrium of the heart thereby creating the possibility that the blood could pass from the right atrium to the left atrium. But the defect size of PFO is usually smaller than that of ASD and the defect will not extend perpendicularly to the septal wall, i.e. left atrial septal defect is not concentric with that of the right atrium. Once the occluder has been placed, it will prevent the thrombus from entering into the left atrium. Furthermore, the atrial septal defect (ASD) is usually larger and requires repair. Currently there are many types endocardiac occlusion devices for treating congenital heart diseases. These occluders are delivered to the desired location by a corresponding catheter.

Mechanical occlusion devices for treating congenital heart diseases have been proposed in the past, some of which are disclosed in Franker et al., Chinese patent application No. 97194488.1; Franker et al., Chinese patent application No. 98808876.2; and Michael et al., Chinese patent application No. 98813470.5. This kind of device includes a support mesh with contractibility and biocompatible materials, and the biocompatible materials are connected to the circumference of the support mesh. The support mesh, which is put into the catheter first, is delivered to the desired location, and then is deployed to close the septal defect. This kind of device is easy to withdraw and has excellent centricity. However, the left disc of this device directly contacts blood, so that it can form thrombus and release harmful metallic elements more easily. Moreover, because the two discs are a whole, they cannot automatically adjust the angle to adapt to the unique anatomy of the patient. Meanwhile, if the left disc is not deployed completely the operation becomes more complicated. In addition, with the existing technique and the operation method, it is very difficult to determine the size and shape of the septal defect precisely, as well as the limit of the waist size, thereby causing many difficulties to physicians, such as selection error, etc. If an oversized device is selected, the occluder will form a cucurbit shape, and result in an imperfect closing effect.

Accordingly, it would be advantageous to provide a reliable occlusion device which can automatically adjust the angle to adapt to the unique anatomy of the patient.

SUMMARY OF THE INVENTION

The present invention provides a reliable occlusion device with adjustable length tether which can adapt the interseptal length of the device to the unique anatomy of the patient. The two discs can attach to the septal defect closely, so they can improve the closing ability. Moreover, thrombus can be reduced because its left disc is covered with membranes and operate more easily.

The present invention provides an occlusion device where the right disc is made from a double-deck wire mesh with contraction function, and the left disc is made from at least two skeletons covered with membranes, and the two discs are adaptively interlocked together by the skeletons passing through the mesh of the right disc.

The middle segment of each skeleton is U shape, and the depths of the U trough are different, so the skeleton can form a plane after being linked together. The skeleton is then covered with membranes to form a disc shape.

The left disc is made from several radially-extending skeletons by heat treatment, and covered with membranes, and the center of each skeleton extends radially after overlapping together.

The two ends of each skeleton are spherical shaped and are wrapped by the membranes, and the ends of the right disc are fixed by a tip or a joint, then the right disc undergoes heat treatment. Then the skeletons pass through the mesh near the tip and are overlapped together. The membranes are made from biocompatible materials.

Furthermore, because the connection of the two discs has gimbal function and the distances between the two discs may expand and contract suitably, the device can adapt to the interseptal length between two discs for the unique anatomy of the patient. Therefore, the two discs may attach to the heart defects closely and increase its closing ability. Moreover, the occlusion device can reduce the thrombus as well as harmful elements because of its left disc being covered with membranes. In addition, the device, which is fission structure, (i.e. its two discs could deploy completely), is easy to operate and increases the closing reliability.

DETAILED DESCRIPTION OF THE INVENTION

Figure 1:
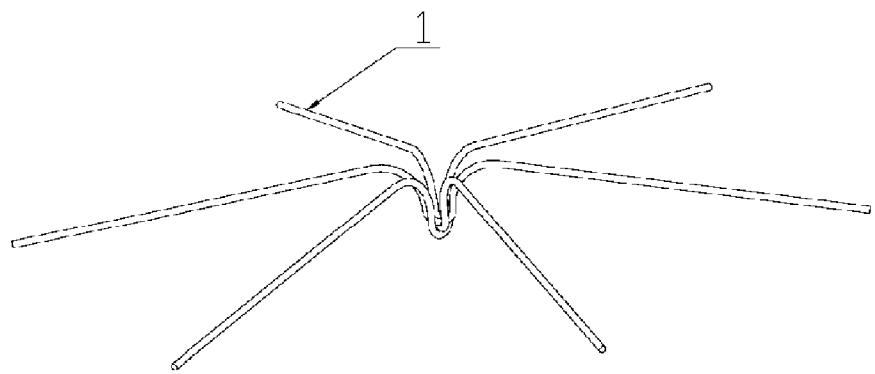
FIG. 1 is a schematic representation of a disc which is constructed by skeletons in accordance with the invention.
Figure 4:
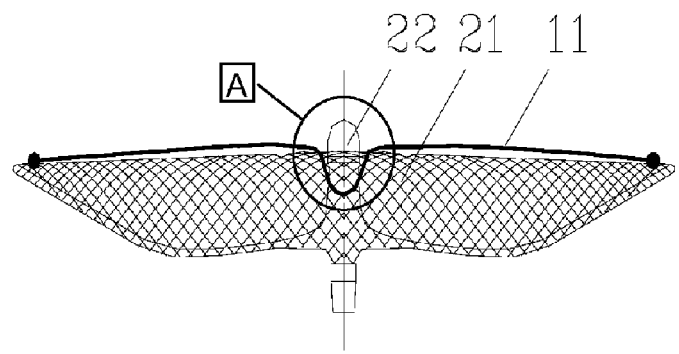
FIG. 4 is a side view of the occlusion device in accordance with the invention.

The present invention provides a heart septal defect occlusion device for occluding an anatomical aperture, such as a patent foramen ovale occluder shown in FIG. 4. The occluder comprises right disc 21 (i.e. metal mesh disc), tip 22, joint 23, left disc 1 which is covered with membranes, and membranes 100, as shown in FIG. 1 and FIG. 9.

Figure 2:
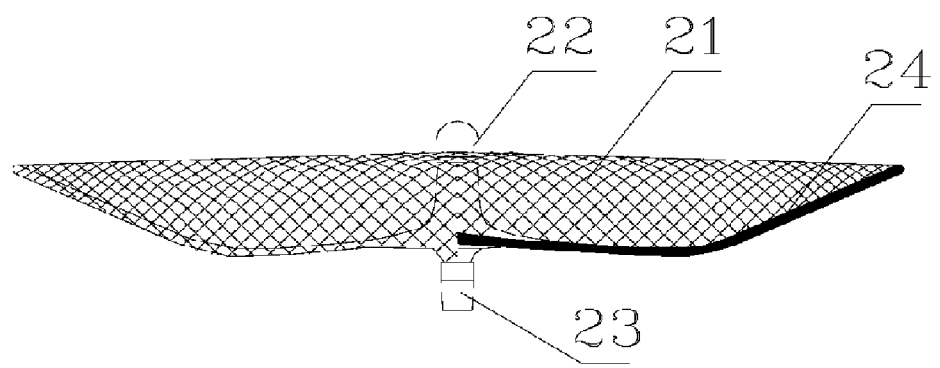
FIG. 2 is a side view of the right disc in accordance with the invention.
Figure 3:
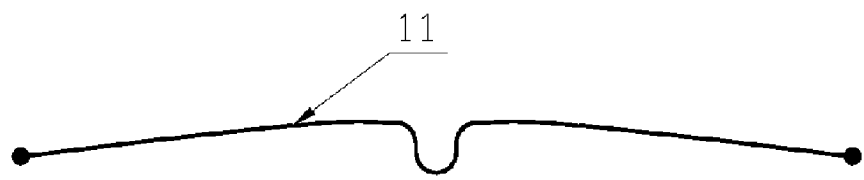
FIG. 3 is a side view of the skeleton in accordance with the invention.
Figure 11:
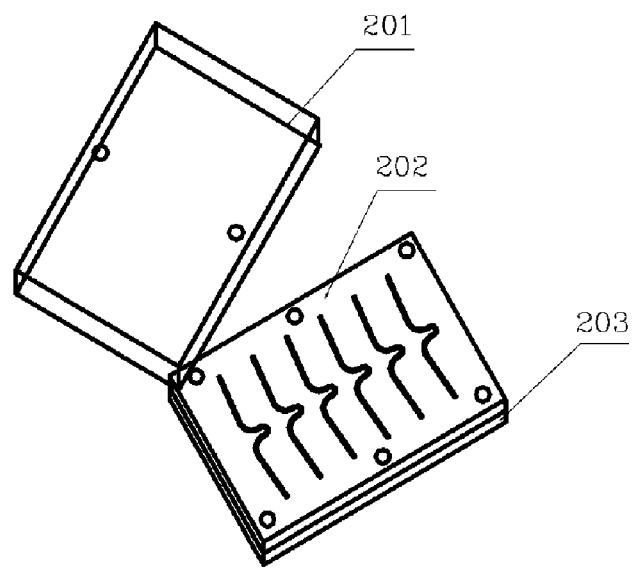
FIG. 11 is a schematic representation of a mould, which is used to heat-treat the skeletons.

The present invention will be described using a PFO occluder as an example. The maximal character of the PFO occluder, when compared with those of the above-referenced patents, is that the left disc 1 comprises six skeletons 11 which are spaced apart evenly. And the six skeletons are linked together in the center and form a radial-extending disc. It is possible that the left disc 1 may comprise at least two skeleton 11 as shown in FIG. 3, and skeleton 11 is made from nitinol wire with shape memory. FIG. 11 illustrates the mould which is used to heat treat skeletons 11; the mould includes upper-mould 201, middle-mould 202 and under-mould 203 and the nitinol wire will be put into the rabbet of the middle-mould 202. By heating the nitinol wire above a certain phase transition temperature, the crystal structure of the nitinol wire can be reset in the austenitic phase, and this will tend to "set" the shape of the device, (i.e., it can keep the shape when it is fixed in the mould). Except for an outside force, the wire can keep the "set" shape even if cooled, and when the outside force is withdrawn, it can resume its original shape. The middle segment of the skeleton 11 is U shape, and the depth of each U trough is different. By providing different depth U troughs for each skeleton 11, these skeletons can form a plane after they have been overlapped together. The skeletons 11 are then covered with membranes to form the left disc 1. The right disc 21 of a PFO occluder uses moulding components. Firstly, the suitable tubular metal mesh of the PFO occluder is formed by weaving or laser carving, then the tubular metal mesh is inserted into the mould and undergoes heat treatment. And, the tip 22 and joint 23 are welded to the disc as shown in FIG. 2.

Figure 5:
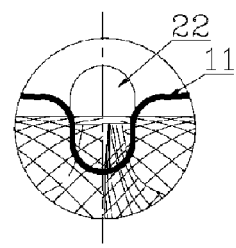
FIG. 5 is an enlarged partial sectional view of part A as shown in FIG. 4.
Figure 6:
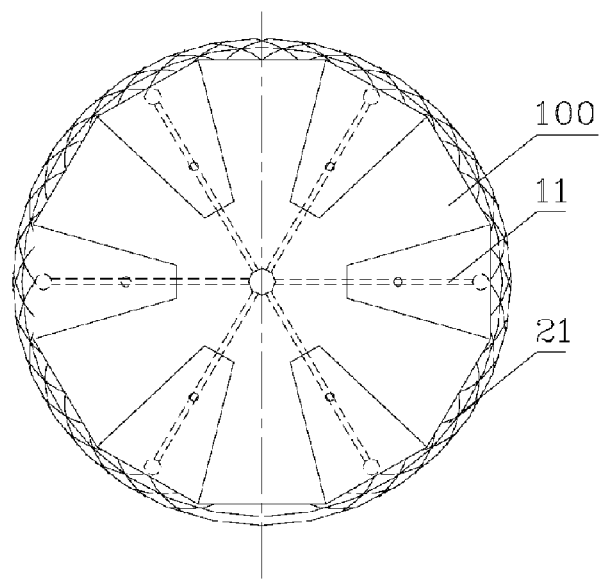
FIG. 6 is a front view of the occlusion device in accordance with the invention.

After the two ends have been welded into spheres respectively, the skeleton 11 as shown in FIG. 3 is passed through the right disc 21 and near the tip 22, and then a double-disc structure is formed as shown in FIG. 5. And as shown in FIG. 6, the skeletons 11 are spaced apart evenly. Accordingly, these skeletons 11 form a metal disc as shown in FIG. 4.

Figure 9:
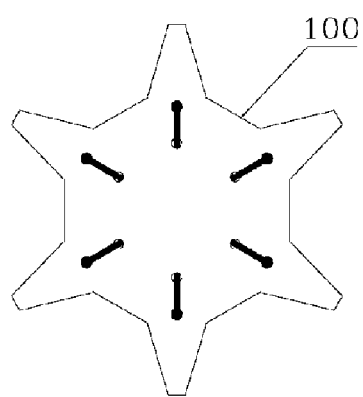
FIG. 9 is a side view of the membrane, which is used to cover the skeletons in accordance with the invention.
Figure 10:
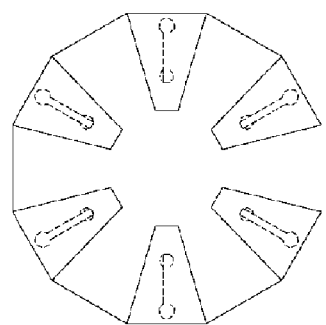
FIG. 10 is a side view of the skeletons, which have been covered with membranes such as shown in FIG. 9.

The two sides of the left disc 1 are covered with membranes 100 as shown in FIG. 9, and FIG. 10 illustrates the skeleton 11 with covered membranes 100. The membranes are made from biocompatible materials. As described above, the spheres of each skeleton are wrapped in the biocompatible materials, so that it can prevent skeleton 11 from puncturing the membranes 100. Another membrane made by biocompatible material 24 is filled into the right disc 21.

Figure 7:
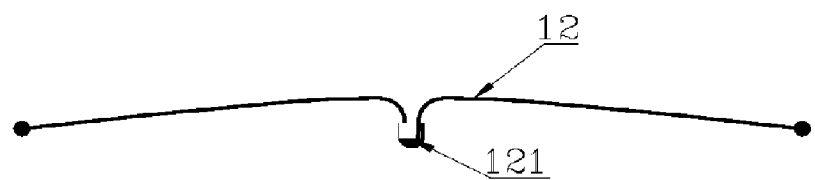
FIG. 7 and FIG. 8 are alternative embodiments of skeletons.
Figure 8:
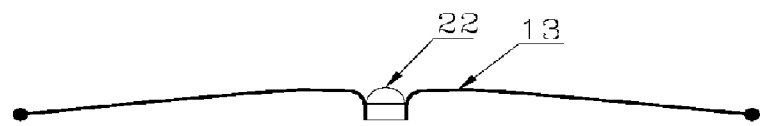

As described above, the overlapping point of left disc 1 is passed through right disc 21, and the connection between the two discs has a gimbal function. Furthermore, the two discs have a trend of shrinking toward the inside, and the occlusion device may swing randomly, i.e., the left disc 1 and right disc 21 may be parallel or be angled. Accordingly, the device can adapt to the unique anatomy in a patient, and the two discs can be attached to the defect closely. Additionally, alternative structure and assembly of the skeleton 11 are shown in FIG. 7 and FIG. 8. FIG. 7 illustrates another embodiment of a skeleton 11 having a plurality of separate spokes 12 connected (e.g., by welding or clamping) to a central cap 121, while FIG. 8 illustrates yet another embodiment where a plurality of spokes 13 are attached directly on a tip 22 which can be the same as the tip 22 shown in FIGS. 2, 4 and 5.

The occlusion device as described above may be extended and put into a catheter, and is delivered to the desired location, then is released. The tapered waist of the device not only ensures its self-centricity but also can reduce the probability of bad occlusion effect resulting from selection error. The left disc 1, which comprises skeletons and membranes, can decrease metal surface areas, thereby decreasing thrombus formation as well as harmful elements. The two discs are both individual components and can deploy completely after release of the occlusion device, and this can avoid forming cucurbit shape and increase the reliability of the desired occlusion.

Figure 12:
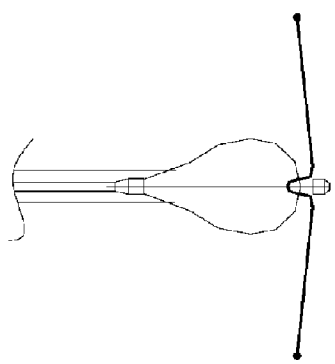
FIG. 12 is a schematic representation of a PFO occluder being released from a delivery catheter.
Figure 13:
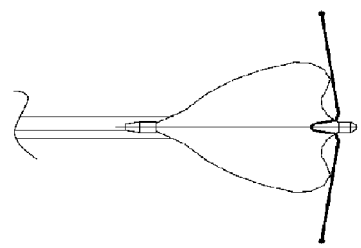
FIG. 13 is a schematic representation of an ASD occluder being released from a delivery catheter.

FIG. 12 and FIG. 13 illustrate the deployment process of an FPO occluder and an ASD occluder during operation respectively. Moreover, the occluder has excellent self-centricity because the right disc 21 is close to the left disc 1.

The present invention is also suitable for treating PDA and VSD etc. The only difference from above other occluders is that the metal mesh of the PDA occluder of the present invention will not form a disc, but a "waist".

Although the description above contains many specificities, these should not be construed as limiting the scope of the invention but as merely providing illustrations of some of the presently preferred embodiments of this invention. Thus the scope of the invention should be determined by the appended claims and their legal equivalents, rather than by the examples given.

What is claimed is:

1. A heart septal defect occlusion device, comprising:
   a right disc made from an interwoven metal mesh, the metal mesh having a plurality of openings;
   a left disc comprising at least two skeletons that are covered by a membrane, with each skeleton passing through some openings of the metal mesh to interlock the right and left discs, wherein the left disc is different from the right disc, wherein each skeleton has a U-shaped middle segment, with the skeletons forming a left disc plane after being assembled together, with the left disc plane covered by the membrane;
   wherein a portion of the right disc lies in the left disc plane, with the U-shaped middle segments interlocked with the metal mesh of the right disc; and
   wherein the right and left discs are individual components that can deploy completely after releasing to avoid forming a cucurbit shape.

2. The device of claim 1, wherein the depth of the U-shaped segments are different for each of the skeletons so that the skeletons form the plane after being interlocked together.

3. The device of claim 2, wherein the left disc is made from at least two radial skeletons.

4. The device of claim 3, wherein the skeletons define two sides, and the skeletons are covered with membranes on both sides.

5. The device of claim 1 wherein the left disc is fixed by a connector.

6. The device of claim 1, wherein the right disc is fixed by a tip or joint.

7. The device of claim 6, wherein the skeletons pass through some openings of the metal mesh near the tip or joint.

8. The device of claim 7, wherein the skeletons overlap each other by passing through some openings of the metal mesh near the tip or joint.

9. The device of claim 1, wherein the membrane is made of biocompatible materials.

10. The device of claim 1, wherein the skeletons are made of a shape-memory material.

11. The device of claim 3, wherein each skeleton has two ends, with each end being spherical.

12. A heart septal defect occlusion device, comprising:

a right disc made from an interwoven metal mesh, the metal mesh having a plurality of openings;

a tip or joint positioned near the center of the right disc;

a left disc comprising at least two skeletons that are covered by a membrane, with each skeleton passing through some openings of the metal mesh near the tip or joint to interlock the right and left discs, each skeleton having two ends, with each end being spherical; and wherein each skeleton has a U-shaped middle segment, with the depth of the U-shaped middle section being different for each of the skeletons so that the skeletons form a left disc plane after being interlocked together, with the left disc plane covered by the membrane, and wherein the left disc is different from the right disc;

wherein a portion of the right disc lies in the left disc plane, with the U-shaped middle segments interlocked with the metal mesh of the right disc; and wherein the right and left discs are individual components that can deploy completely after releasing to avoid forming a cucurbit shape.

13. The device of claim 12, wherein the membrane is made of biocompatible materials.

14. The device of claim 13, wherein the skeletons are made of a shape-memory material.

15. A heart septal defect occlusion device, comprising:

a right disc comprising a metal mesh that has a plurality of openings, the metal mesh made from a tubular metal mesh that has been formed and then inserted into a mold for heat treatment; and a left disc comprising at least two skeletons that are covered by a membrane, with each skeleton passing through some openings of the metal mesh to interlock the right and left discs, wherein the left disc is different from the right disc;

wherein the right and left discs are individual components that can deploy completely after releasing to avoid forming a cucurbit shape.

16. The device of claim 15, wherein the tubular metal mesh is laser carved.

17. The device of claim 15, wherein the tubular metal mesh is woven.

* * * * *